US010486023B1

(12) United States Patent
Cole et al.

(10) Patent No.: US 10,486,023 B1
(45) Date of Patent: Nov. 26, 2019

(54) METHOD TO EXERCISE AND COORDINATE BOTH THE HANDS AND/OR FEET

(71) Applicants: James Winter Cole, Richardson, TX (US); Alfred M. Saleh, Richardson, TX (US)

(72) Inventors: James Winter Cole, Richardson, TX (US); Alfred M. Saleh, Richardson, TX (US)

(*) Notice: Subject to any disclaimer, the term of this patent is extended or adjusted under 35 U.S.C. 154(b) by 0 days.

(21) Appl. No.: 16/199,165

(22) Filed: Nov. 24, 2018

Related U.S. Application Data (63) Continuation-in-part of application No. 15/711,245, filed on Sep. 21, 2017, now abandoned.

(51) Int. Cl.
| | |
|---|---|
| *A63B 24/00* | (2006.01) |
| *G09B 5/02* | (2006.01) |
| *A61B 3/00* | (2006.01) |
| *A61B 5/16* | (2006.01) |
| *G06F 3/033* | (2013.01) |
| *G16H 20/30* | (2018.01) |
| *A61B 5/11* | (2006.01) |
| *G09B 19/00* | (2006.01) |

(52) U.S. Cl.
CPC ........ *A63B 24/0006* (2013.01); *A61B 3/0033* (2013.01); *A61B 3/0041* (2013.01); *A61B 5/1124* (2013.01); *A61B 5/162* (2013.01); *G06F 3/0334* (2013.01); *G09B 5/02* (2013.01); *G16H 20/30* (2018.01); *G06F 2203/0382* (2013.01); *G09B 19/00* (2013.01)

(58) Field of Classification Search
CPC ............. G06F 2230/0382; G06F 3/033; G06F 3/0334; A61B 5/16; A61B 5/162; A61B 5/4088; A61B 3/0033; A61B 3/0041; A61B 5/1124; A61B 5/74; A61B 5/742; G09B 7/00; G09B 19/00; G09B 5/02; G16H 20/30; A63F 13/212; A63B 24/0006; A63B 2024/0009
See application file for complete search history.

(56) References Cited

U.S. PATENT DOCUMENTS

| | | | | |
|---|---|---|---|---|
| 6,632,174 | B1 * | 10/2003 | Breznitz | A61B 5/16 434/236 |
| 2006/0066571 | A1 * | 3/2006 | Fairs | G06F 3/038 345/157 |
| 2009/0305207 | A1 * | 12/2009 | Ueshima | A63B 24/0003 434/258 |

(Continued)

*Primary Examiner* — John Villecco (57) ABSTRACT

A method of coordinating and exercising the extremities of a person by the independent and/or simultaneous gestures of both the hands and feet. The method comprises the computer, four USB ports and four wired and/or wireless mice that correspond to the four-cursor exponential cognitive human-man-interface (HMI) exercise application The HMI application will instruct the person to begin tracing each of the four cursors on separate tracks in the pattern towards a desired target by the gestures of both the hands and the feet (extremities), which are appended to the mice. Displaying the performance data of each extremity including time, distance, and speed measures the competitiveness of both the hands and the feet against each other. The goal is for the left-hand, right-hand, left-foot and right foot to reach the target at the same time at the fastest speed possible.

3 Claims, 8 Drawing Sheets

(56) References Cited

U.S. PATENT DOCUMENTS

| | | | | |
|---|---|---|---|---|
| 2014/0107429 A1* | 4/2014 | Simkovich | ............... | A61B 5/16 600/300 |
| 2014/0330159 A1* | 11/2014 | Costa | ................... | A61B 5/1124 600/558 |
| 2017/0025033 A1* | 1/2017 | Rath | ...................... | A61B 5/103 |

* cited by examiner

Level 1

Left Hand

Right Hand

Objective: Simultaneously and independently move the cursors from each corner of the screen to the middle square by using your left hand, right hand, left foot and right foot.

Left Foot

Right Foot

Level 6

Objective:

Simultaneously and independently move the cursors (  ) in each star in the same direction of the arrows, from the Start point.

Figure 6

Level 7
Objective:
Simultaneously and independently move the cursors ( ➡ ) in each star in the same direction of the arrows, from the Start point.

METHOD TO EXERCISE AND COORDINATE BOTH THE HANDS AND/OR FEET

BACKGROUND OF THE INVENTION

In most commercial and residential computer applications, USB ports can be assigned to multiple control devices (e.g. mice, joy sticks) that manage independently one or two computerized cursors but not simultaneously. Hence, the novelty of the invention is moving four cursors simultaneously and/or independently on a computer screen by using a cognitive human-man-interface (HMI) exercise application that maps four computerized cursors against four USB ports that correspond to the gestures of the left-hand, right-hand, left-foot and right-foot which are appended to mice.

BRIEF SUMMARY OF THE INVENTION

A method to exercise and coordinate the simultaneous and/or independent physical gestures of the left-hand, right-hand, left-foot and right-foot (herein sometimes called extremities) which are appended to mice. The objective of the method is to simultaneously and/or independently move and trace the four computerized cursors on separate tracks in a pattern, to arrive at a target at the same time by the gestures of the left-hand, right-hand, left-foot and right-foot. The HMI exercise application displays four mice counter windows on the computer screen that displays the performance data (speed, path deviation, time) of the extremities to enable the person to view the competitiveness of the extremities against each other during and after the exercise and adjust accordingly for the next level of exercise.

DETAILED DESCRIPTION AND BEST MODE OF IMPLEMENTATION

This is a continuation in part (CIP) of application Ser. No. 15/711,245 which is incorporated herein by references of entry.

Figure 7:
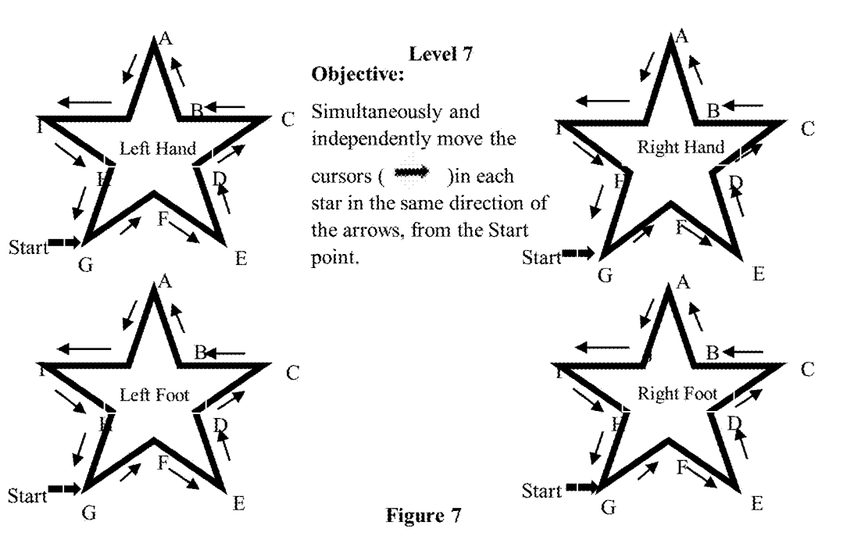
Figure 8:
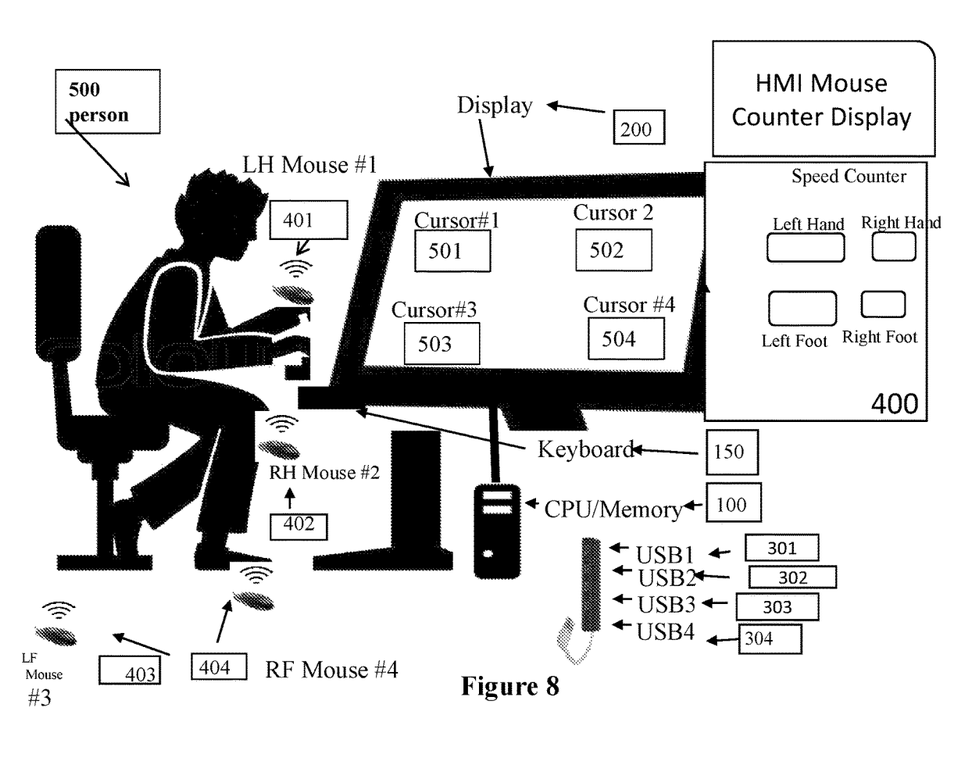

The following information references numerical identifiers in FIG. 8. A new innovative method to exercise and coordinate a person's (500) cognitive ability on a computer (100) display screen (200) by the simultaneous and/or independent physical gestures of both the hands and the feet (extremities) of the person (500). The embodiment of the invention comprises the computer display/screen (200), keyboard (150), the four dedicated USB ports (301-304), the four wired and/or wireless control devices, herein called mice (401-404); and a human-man-interface (HMI) cognitive/exercise application (200 and 400) with four assignable computerized cursor drivers (501-504), four mice performance data counters (400) and seven exercise templates at various skill levels (FIG. 1-7). When the person (500) turns on the computer (100), clicks on the HMI icon application (200, 400) and selects one of the seven exercise templates (FIGS. 1-7) the person (500) can begin tracing the four cursors (501-504) at the same time from a starting-point to an end-point on four separate paths on a template simultaneously and/or independently from the gestures of the extremities. The objective of the method is to simultaneously and/or independently move the four cursors from the starting-point (FIG. 1-7) to arrive at the end-point (FIG. 1-7) at the same time at fastest speed possible. The following describes the integration of the computer and the HMI application.

The computer comprises (100) 1) integrated standard computer screen and/or touch screen or extended display (200); 2) integrated computer keyboard or wired and/or wireless keyboard (150); 3) the four dedicated USB ports (301-304), and 4) the four wired and/or wireless mice (401-404). The mouse (401-404) is appended to one of the extremities of the person and assigned the USB port and one of the four colored cursors; left-hand mouse #1 (401) is assigned USB port 1 (301) with a blue blinking cursor (501); right-hand mouse #2 (402) is assigned USB port 2 (302) with a green blinking cursor (502); left-foot mouse #3 (403) is assigned USB port 3 (303) with a yellow blinking cursor (503); and right-foot mouse #4 (404) is assigned USB port 4 (304) with a red blinking cursor (504).

The exercise begins once the person turns on the computer, clicks on the HMI exercise application icon on the computer display screen and subsequently selects one of the seven exercise templates (levels) as depicted in FIGS. 1-7. Once the exercise template is selected the application will display the pattern for the cursor to traverse. Concurrently, the HMI application will assign the blinking color cursors that correspond to the four USB ports which are mapped to the four mice that are appended to the person's extremities. The cursor assignment is discussed in the following format:

HMI left-hand Cursor Driver #1 (501)
    assigns the blue blinking cursor #1 to USB port 1
    records and displays the performance data of the left-hand mouse (400):
        cursor #1 speed counter display (number of pixels in the pattern divided by time); tracks and records the speed of cursor #1 on a linear path in the pattern from the starting-point to the end-point for the person to compare cursor #1 speed against the speed of the other three cursors which allows the person to adjust the physical gestures of the extremities to move the four cursors to reach the end-point at the fastest speed possible.

Cursor #1 pattern deviation counter display (total number of pixels in the pattern minus the total number of pixels deviated from the pattern divided by the total number of pixels); tracks and records cursor #1 path deviation on a linear path in the pattern from the starting-point to the end-point for the person to compare cursor #1 deviation against the path deviation of the other three cursors which allows the person to adjust the physical gestures of the extremities accordingly to improve performance.

Cursor #1 accuracy counter display (speed multiplied by deviation in the pattern); determines cursor #1 overall performance characteristics on a linear path in the pattern from the starting-point to the end-point which allows the person to compare cursor #1 movement against the movement of the other three cursors and adjust accordingly to improve the person's performance.

left-hand mouse #1 performance data results are displayed at the top left in the left-hand pattern (FIGS. 1-7 and FIG. 8 200, 400)

HMI right-hand Cursor Driver #2 (502)
assigns the green blinking cursor #2 to USB port 2
records and displays the performance data of the right-hand mouse (401):

cursor #2 speed counter display (number of pixels divided by time); tracks and records the speed of cursor #1 on a linear path in a pattern from the starting-point to the end-point for the person to compare cursor #1 speed against the speed of the other three cursors which allows the person to adjust the physical gestures of the extremities to move the four cursors to reach the end-point at the fastest speed possible.

Cursor #2 pattern deviation counter display (total number of pixels in a pattern minus the total number of pixels deviated from the pattern divided by the total number of pixels); tracks and records cursor #2 path deviation on a linear path in the pattern from the starting-point to the end-point for the person to compare cursor #2 deviation against the path deviation of the other three cursors which allows the person to adjust the physical gestures of the extremities accordingly to improve performance.

Cursor #2 accuracy counter display (speed multiplied by deviation in a pattern); determines cursor #2 overall performance characteristics on a linear path in the pattern from the starting-point to the end-point which allows the person to compare cursor #2 movement against the movement of the other three cursors and adjust accordingly to improve the person's performance.

Right-hand mouse #2 performance data results are displayed at the top right in the right-hand pattern (FIGS. 1-7 and FIG. 8 200, 400).

HMI left-foot Cursor Driver #3 (503)
assigns the red blinking cursor #3 to USB port 3
records and displays the performance data of the left-foot mouse (403):

cursor #3 speed counter display (number of pixels divided by time in the pattern); tracks and records the speed of cursor #3 on a linear path in a pattern from the starting-point to the end-point for the person to compare cursor #3 speed against the speed of the other three cursors which allows the person to adjust the physical gestures of the extremities to move the four cursors to reach the end-point at the fastest speed possible.

Cursor #3 pattern deviation counter display (total number of pixels in a pattern minus the total number of pixels deviated from a pattern divided by the total number of pixels); tracks and records cursor #3 path deviation on a linear path in the pattern from the starting-point to the end-point for the person to compare cursor #3 deviation against the path deviation of the other three cursors which allows the person to adjust the physical gestures of the extremities accordingly to improve performance.

Cursor #3 accuracy counter display (speed multiplied by deviation in a pattern); determines cursor #3 overall performance characteristics on a linear path in the pattern from the starting-point to the end-point which allows the person to compare cursor #3 movement against the movement of the other three cursors and adjust accordingly to improve the person's performance.

left-foot mouse #3 performance data results are displayed at the top left in the left-foot pattern (FIGS. 1-7 and FIG. 8 200, 400).

HMI right-foot Cursor Driver #4 (504)
assigns the yellow blinking cursor #4 to USB port 4
records and displays the performance data of the right-foot mouse (404):

cursor #4 speed counter display (number of pixels divided by time in a pattern); tracks and records the speed of cursor #4 on a linear path in the pattern from the starting-point to the end-point for the person to compare cursor #4 speed against the speed of the other three cursors which allows the person to adjust the physical gestures of the extremities to move the four cursors to reach the end-point at the fastest speed possible.

Cursor #4 pattern deviation counter display (total number of pixels in a pattern minus the total number of pixels deviated from a pattern divided by the total number of pixels); tracks and records cursor #4 path deviation on a linear path in the pattern from the starting-point to the end-point for the person to compare cursor #4 deviation against the path deviation of the other three cursors which allows the person to adjust the physical gestures of the extremities accordingly to improve performance.

Cursor #4 accuracy counter display (speed multiplied by deviation in a pattern); determines cursor #4 overall performance characteristics on a linear path in the pattern from the starting-point to the end-point which allows the person to compare cursor #4 movement against the movement of the other three cursors and adjust accordingly to improve the person's performance.

Right-foot mouse #4 performance data results are displayed at the top right in a right-foot pattern (FIGS. 1-7 and FIG. 8 200, 400).

The following explains how the person exercises and coordinates cognitive abilities by using the exercise pattern on a template (levels) as depicted in FIGS. 1-8. The person inserts the HMI cognitive application CD in the computer. After initialization, the HMI exercise pattern application icon appears on the computer display for the person to click on which subsequently instructs the person to select one of the seven exercise templates (FIGS. 1-7) to begin the cognitive exercise. After selection of the desired exercise template the person appends the left-hand mouse #1 to the left-hand, the right-hand mouse #2 to the right-hand, the left-foot mouse #3 to the left-foot and the right-foot mouse #4 to the right-foot. After appending the mouse to each extremity of the person, the HMI application on the computer screen presents the person with four colored blinking cursors (blue, green, yellow and red) within the pattern in the template. A colored blinking cursor is displayed in each corner in the pattern on the computer screen; a blinking left-hand blue cursor #1 is displayed at the top left of the pattern; a blinking right-hand green cursor #2 is displayed at the top right of the pattern; a blinking left-foot yellow cursor #3 is displayed at the bottom left of the pattern and a blinking right-foot red cursor #4 is displayed at the bottom right of the pattern. Concurrently with the appearance of the blinking cursor in the pattern, a blinking message "start exercise pattern application is displayed: YES or NO" is presented to the person. After clicking on YES, the exercise application for cognitive ability is ready and the person begins tracing the four cursors in the pattern by the simultaneous and/or independent gestures of the left-hand, right-hand, left-foot and right-foot and foot that corresponds to the four The HMI cognitive application records and displays the cursor performance data (speed, path deviation, and accuracy) from the starting-point, to the end-point in the selected pattern for the person to compare the competitiveness of each extremity against the other. The challenge is for the extremities (left-hand, right-hand, left-foot, right-foot) to move the four cursors at the same time from a starting-point to an end-point at the fastest speed possible. The following describes the specific functionality of the seven cognitive exercise pattern templates.

Figure 1:
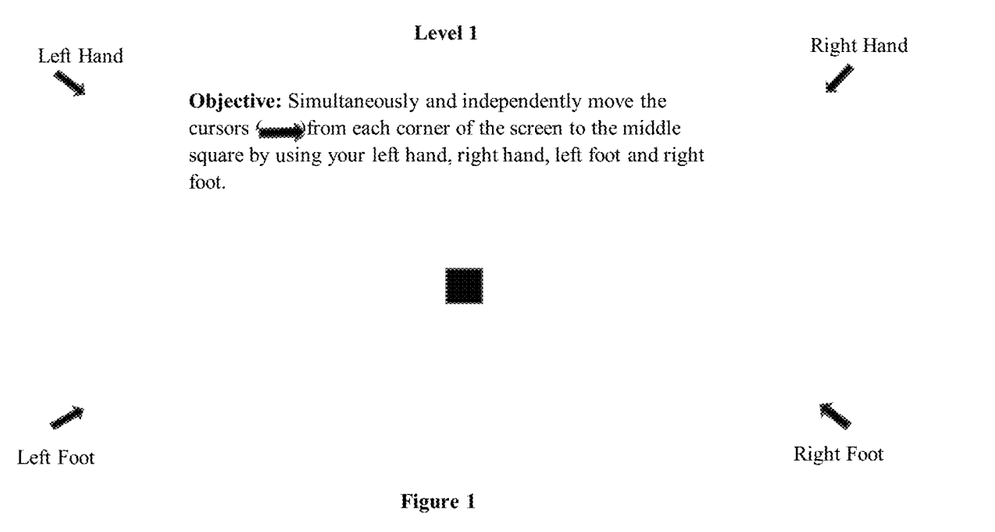
FIG. 1. Simultaneously and/or independently move the cursors from each corner of the screen to the middle square by using the left-hand, right-hand, left-foot and right-foot.

FIG. 1 template (level 1) illustrates a template with an exercise pattern with the four two-dimensional colored blinking computerized cursors that are located at each corner of the pattern (screen) which is displayed on the computer screen by the human-man interface (HMI) exercise pattern template application. The pattern corner is the starting-point for the colored blinking cursor. At the center of the pattern (screen) is the end-point (target). Once a person appends the mice to the extremities as discussed in paragraph [0015], clicks on the HMI exercise pattern application icon, chooses the exercise pattern template, clicks on 'YES' from a displayed ready message the person can start to move or trace the cursor in the pattern from the starting-point towards the block in the center of the pattern (screen), which is the end-point (target), by the simultaneous and/or independent physical gestures of the extremities (left-hand, right-hand, left-foot, right-foot). The person's extremities move: the top left blue cursor in the pattern by the left-hand towards the block in the pattern's center screen (target); the top right green cursor in the pattern by the right-hand towards the block in the pattern's center screen (target); the bottom left yellow cursor in the pattern by the left-foot towards the block in the pattern's center screen (target), and the bottom right red cursor in the pattern by the right-foot towards the block in the pattern's center screen (target). Only the speed results are displayed in the pattern after the four cursors have arrived at the center pattern (screen), ideally at the same time. The displayed speed results of the cursors allow a person to compare the competitiveness of the extremity against the other. Repeating the exercise improves the speed results of the extremity against the others and prepares the person for the next exercise template which employs a different pattern and skill set.

Figure 2:
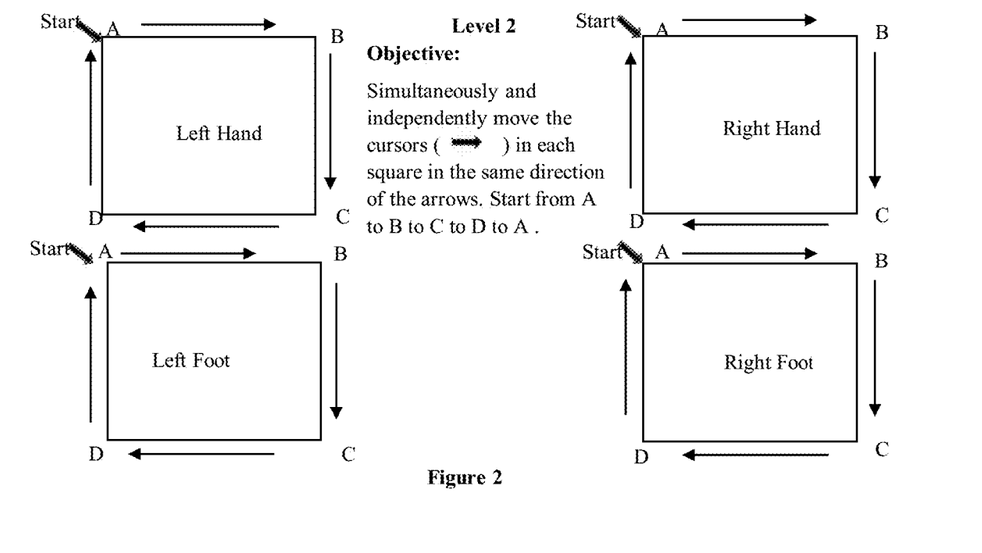
FIG. 2. Simultaneously and/or independently move the cursors in each square in the same direction of the arrows by using the left-hand, right-hand, left-foot and right-foot; Start from A to B to C to D to A.

FIG. 2 template (level 2) illustrates the template with four identical rectangular exercise patterns with an equal number of pixels that are displayed on the computer screen by the HMI exercise pattern application. The pattern is for the left-hand, the pattern is for the right-hand, the pattern is for the left-foot and the pattern is for the right-foot. The pattern displays the two-dimensional colored blinking computerized cursors which is located at the top left of the pattern and a specific path for the cursor to traverse. The cursor path in the pattern traverses horizontally (left to right) from the starting-point 'A' to midpoint 'B'; downwards from midpoint 'B' to midpoint 'C'; horizontally (right to left) from midpoint 'C' to midpoint 'D'; and upwards from midpoint 'B' to the end-point 'A' (formerly starting-point 'A'). Once the person appends the mice to the extremities as discussed in paragraph [0015], clicks on the HMI exercise pattern template application icon, chooses the exercise pattern template and selects a displayed ready message 'YES', activates the exercise application for cognitive abilities. After activation of the pattern application, a person can now start to simultaneously and/or independently move the top left cursor in the pattern from starting-point 'A' to the ending-point 'A' by the physical gestures of the extremities (both the hands and the feet). When FIG. 2 template application is activated, and the person appends the mice to the extremities, the person can:

Reference left-hand rectangular pattern: move blue blinking cursor #1, located at the top left of the left-hand rectangular pattern, horizontally (left to right) on a marked linear path from starting point 'A' to midpoint 'B'; downward on a marked linear path from midpoint 'B' to midpoint 'C'; horizontally (right to left) on a marked linear path from midpoint 'C' to midpoint 'D'; and upward on a marked linear path from midpoint 'D' to the end-point 'A' (formerly starting-point 'A').

Reference right-hand rectangular pattern: move green blinking cursor #2, located at the top left of the right-hand rectangular pattern, horizontally (left to right) on a marked linear path from starting-point 'A' to midpoint 'B'; downward on a marked linear path from midpoint 'B' to midpoint 'C'; horizontally (right to left) on a marked linear path from midpoint 'C' to midpoint 'D'; and upward on a marked linear path from midpoint 'D' to the end-point 'A' (formerly starting-point 'A').

Reference left-foot rectangular pattern: move yellow blinking cursor #3, located at the top left of the left-foot rectangular pattern, horizontally (left to right) on a marked linear path from starting point 'A' to midpoint 'B'; downward on a marked linear path from midpoint 'B' to midpoint 'C'; horizontally (right to left) on a marked linear path from midpoint 'C' to midpoint 'D'; and upward on a marked linear path from midpoint 'D' to the end-point 'A' (formerly starting-point 'A').

Reference right-foot rectangular pattern: move red blinking cursor #4, located at the top left of the left-foot rectangular pattern, horizontally (left to right) on a marked linear path from starting point 'A' to midpoint 'B'; downward on a marked linear path from midpoint 'B' to midpoint 'C'; move horizontally (right to left) on a marked linear path from midpoint 'C' to midpoint 'D'; and upward on a marked linear path from midpoint 'D' to the end-point 'A' (formerly starting-point 'A').

A person can simultaneously and/or independently move the four computerized cursors by the physical gestures of both the hands and the feet (extremities). A display counter will record and display the speed, deviation and accuracy of the extremity in the pattern. The performance data (speed, deviation and accuracy) results are displayed in the pattern during and after the cursor arrives at the ending-point 'A', ideally, at the same time. The displayed results of the cursor allow the person to compare the competitiveness of the extremity against the other. Repeating the exercise improves the speed results of the extremity and prepares the person for the next exercise template which employs a different pattern and different set.

Figure 3:
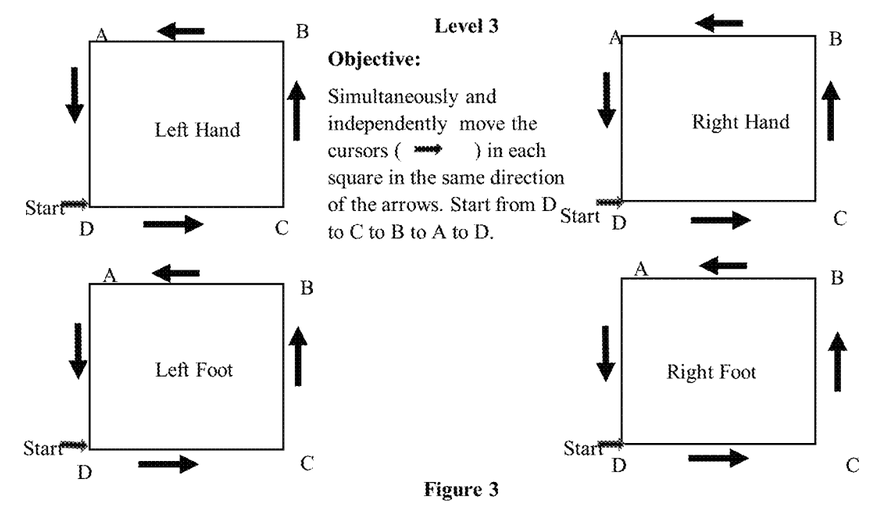
FIG. 3. Simultaneously and/or independently move the cursors in each square in the same direction of the arrows by using the left-hand, right-hand, left-foot and right-foot; Start from D to C to B to A to D.

FIG. 3 template (level 3) illustrates a template with four identical rectangular exercise patterns with an equal number of pixels that is displayed on the computer screen by the HMI exercise pattern application. The pattern is for the left-hand; the pattern is for the right-hand; the pattern is for the left-foot and the pattern is for the right-foot. The pattern displays a two-dimensional colored blinking computerized cursor which is located at the top left of the pattern and a specific path for the cursor to traverse. The cursor path in the pattern traverses horizontally (left to right) from the starting-point 'D' to midpoint 'C'; upwards from midpoint 'C' to midpoint 'B', horizontally (right to left) from midpoint 'B' to midpoint 'A'; and downward from midpoint 'A' to the end-point 'D' (formerly starting-point 'D). Once the person appends the mice to the extremities, as discussed in paragraph [0015], clicks on the HMI exercise pattern application icon, chooses the exercise pattern template application, selects the displayed ready message 'YES', activates the exercise application of cognitive abilities. After activation of the exercise pattern application, the person can now start to simultaneously and/or independently move the bottom left cursor in the pattern from starting point 'D' to the ending-point 'D' by the physical gestures of the extremities (both the hands and the feet). When FIG. 3 template application is activated, and the person appends the mice to the extremities, the person can:

Reference left-hand rectangular pattern: move blue blinking cursor #1, located at the bottom left of the left-hand rectangular pattern, horizontally (left to right) on a marked linear path from starting point 'D' to midpoint 'C'; upward on a marked linear path from midpoint 'C' to midpoint 'B'; horizontally (right to left) on a marked linear path from midpoint 'B' to midpoint 'A'; and downward on a marked linear path from midpoint 'A' to the end-point 'D' (formerly the starting-point 'D').

Reference right-hand rectangular pattern: move green blinking cursor #2, located at the bottom left of the left-hand rectangular pattern, horizontally (left to right) on a marked linear path from starting-point 'D' to midpoint 'C'; downward on a marked linear path from midpoint 'C to midpoint 'B'; horizontally (right to left) on a marked linear path from midpoint 'B' to midpoint 'A'; and downward on a marked linear path from midpoint 'A' to the end-point 'D' (formerly starting-point 'D').

Reference left-foot rectangular pattern: move yellow blinking cursor #3, located at the bottom left of the left-hand rectangular pattern, horizontally (left to right) on a marked linear path from starting point 'D' to midpoint 'C'; downward on a marked linear path from midpoint 'C' to midpoint 'B'; horizontally (right to left) on a marked linear path from midpoint 'B' to midpoint 'A'; and downward on a marked linear path from midpoint 'A' to the end-point 'D' (formerly starting-point 'A').

Reference right-foot rectangular pattern: move red blinking cursor #4, located at the bottom left of the left-hand rectangular pattern, horizontally (left to right) on a marked linear path from starting-point 'D' to midpoint 'C'; upward on a marked linear path from midpoint 'C to midpoint 'B'; horizontally (right to left) on a marked linear path from midpoint 'B' to midpoint 'A'; and downward on a marked linear path from midpoint 'A' to the end-point 'D' (formerly the starting-point 'D').

The person can simultaneously and/or independently move the four computerized cursors by the physical gestures of both the hands and the feet (extremities). A display counter will record and display the speed, deviation and accuracy of the extremity in the pattern. The performance data (speed, deviation and accuracy) results are displayed in the pattern after the cursor arrives at the ending-point 'D', ideally, at the same time. The displayed results of the cursor allow the person to compare the competitiveness of the extremity against the other. Repeating the exercise improves the speed results of the extremity against the other and prepares the person for the next exercise template which employs a different pattern and skill set.

Figure 4:
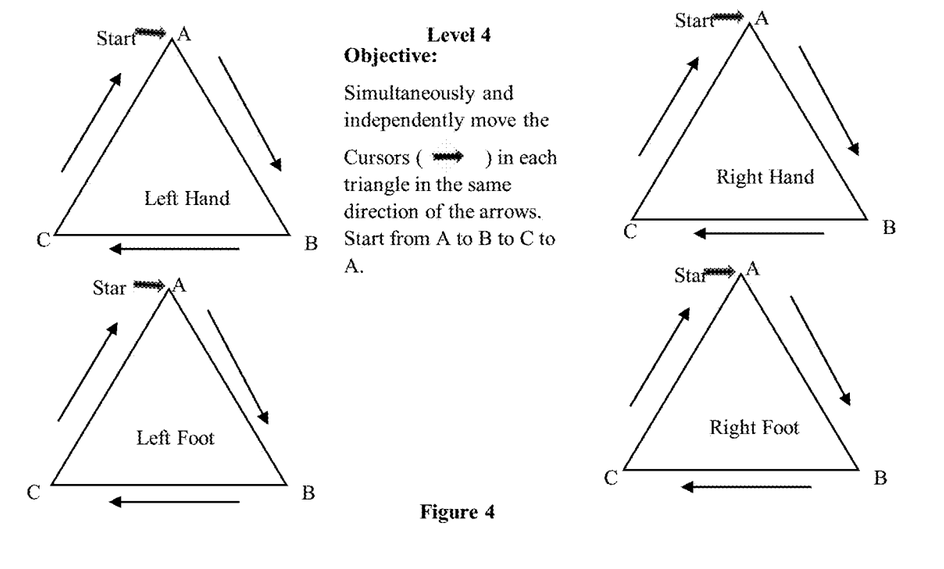
FIG. 4. Simultaneously and/or independently move the cursors in each triangle in the same direction of the arrows by using the left-hand, right-hand, left-foot, and right-foot; Start from A to B to C to A.

FIG. 4 template (level 4) illustrates the template with four identical triangular exercise patterns with an equal number of pixels that is displayed on the computer screen by the HMI exercise pattern application. The pattern is for the left-hand; the pattern is for the right-hand; the pattern is for the left-foot; and the pattern is for the right-foot. The pattern displays a two-dimensional colored blinking computerized cursor which is located at the top angle 'A' of the pattern, and a specific path for the cursor to traverse. The cursor path in each triangular pattern traverses from a starting-point angle 'A' to midpoint angle 'B'; from midpoint angle 'B' to midpoint angle 'C'; and midpoint angle 'C' to the end-point angle 'A' (formerly starting-point angle 'A'). The person appends the mice to the extremities as discussed in paragraph [0015], clicks on the HMI exercise pattern application icon, chooses the exercise template application and selects the displayed ready message 'YES', to activate the exercise application of cognitive abilities. After activation of the pattern application, the person can now start to simultaneously and/or independently move the top angle 'A' cursor in the pattern from a starting point angle 'A' to the ending-point angle 'A' by the physical gestures of the person's extremities. When FIG. 4 template application is activated, and the person appends the mice to the extremities, the person can:

Reference left-hand triangular pattern: move blue blinking cursor #1, located at top angle 'A' of the left-hand triangular pattern, on a marked linear path from starting point angle 'A' to midpoint angle 'B'; from midpoint angle 'B' on a marked linear path to midpoint angle 'C'; and from midpoint angle 'C' on a marked linear path to the end-point angle 'A' (formerly starting-point angle 'A').

Reference right-hand triangular pattern: move green blinking cursor #2, located at the top angle 'A' of the right-hand triangular pattern, on a marked linear path from starting-point angle 'A' to midpoint angle 'B'; from midpoint angle 'B' on a marked linear path to midpoint angle 'C'; and from midpoint angle 'C' on a marked linear path to the end-point angle 'A' (formerly the start-point angle 'A').

Reference left-foot triangular pattern: move yellow blinking cursor #3, located at the top angle 'A' of the left-foot triangular pattern, on a marked linear path from starting-point angle 'A' to midpoint angle 'B'; from midpoint angle 'B' on a marked linear path to midpoint angle 'C'; and from midpoint angle 'C' on a marked linear path to the end-point angle 'A' (formerly the start-point angle 'A').

Reference right-foot triangular pattern: move red blinking cursor #4, located at the top angle 'A' of the right-foot triangular pattern, on a marked linear path from starting-point angle 'A' to midpoint angle 'B'; from midpoint angle 'B' on a marked linear path to midpoint angle 'C'; and from midpoint angle 'C' on a marked linear path to the end-point angle 'A' (formerly the start-point angle 'A').

The person can simultaneously and/or independently move the computerized cursors by the physical gestures of both the hands and the feet (extremities). The display counter will record and display the speed, deviation and accuracy of the extremity in a pattern. The performance data (speed, deviation and accuracy) results are displayed in the pattern during and after the cursor arrives at the ending-point angle 'A', ideally, at the same time. The displayed results of the cursor allow the person to compare the competitiveness of the extremity against the other. Repeating the exercise improves the speed results of the extremity and prepares the person for the next exercise template which employs a different pattern and skill set.

Figure 5:
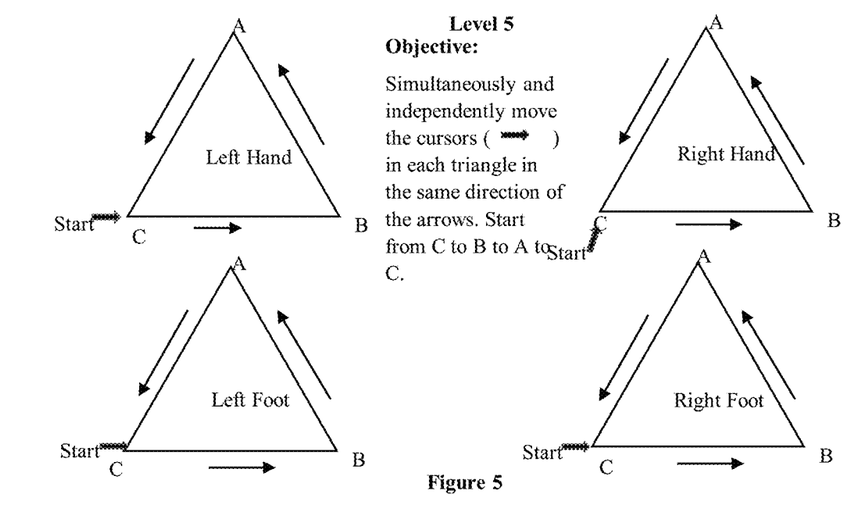
FIG. 5. Simultaneously and/or independently move the cursors in each triangle in the same direction of the arrows by using the left-hand, right-hand, left-foot and right-foot; Start from C to B to A to C.

FIG. 5 template (level 5) illustrates a template with four identical triangular exercise patterns with an equal number of pixels that are displayed on the computer screen by the HMI exercise pattern application. The pattern is for the left-hand, the pattern is for the right-hand, the pattern is for the left-foot and the pattern is for the right-foot. The pattern displays a two-dimensional colored blinking computerized cursor which is located at angle ('C') of the pattern, and a specific path for the cursor to traverse. The cursor path in each triangular pattern traverses from the starting-point angle 'C' to midpoint angle 'B'; from midpoint angle 'B' to midpoint angle 'A'; and midpoint angle 'A' to the end-point angle 'C' (formerly starting-point angle 'C'). Once the person appends the mice to the extremities as discussed in paragraph [0015], clicks on the HMI exercise pattern application icon, chooses the exercise template application and selects the displayed ready message 'YES', activates the exercise application of cognitive abilities. After activation of the pattern application, the person can now start to simultaneously and/or independently move starting-point angle 'C' cursor in the pattern from starting-point angle 'C' to the ending-point angle 'C' by the physical gestures of the extremities. When FIG. 5 template application is activated, and the person appends the mice to the extremities, the person can:

Reference left-hand triangular pattern: move blue blinking cursor #1, located at left angle 'C' of the left-hand triangular pattern, on a marked linear path from starting-point angle 'C' to midpoint angle 'B'; from midpoint angle 'B' on a marked linear path to midpoint angle 'A'; and from midpoint angle 'A' on a marked linear path to the end-point angle 'C' (formerly starting-point angle 'C').

Reference right-hand triangular pattern: move green blinking cursor #2, located at left angle 'C' of the right-hand triangular pattern, on a marked linear path from starting-point angle 'C' to midpoint angle 'B'; from midpoint angle 'B' on a marked linear path to midpoint angle 'A'; and from midpoint angle 'A' on a marked linear path to the tend-point angle 'C' (formerly the start-point angle 'C').

Reference left-foot triangular pattern: move yellow blinking cursor #3, located at the left angle 'C' of the left-foot triangular pattern, on a marked linear path from starting-point angle 'C' to midpoint angle 'B'; from midpoint angle 'B' on a marked linear path to midpoint angle 'A'; and from midpoint angle 'A' on a marked linear path to the end-point angle 'C' (formerly the start-point angle 'C').

Reference right-foot triangular pattern: move red blinking cursor #4, located at the left angle 'C' of the right-foot triangular pattern on a marked linear path from starting-point angle 'C' to midpoint angle 'B'; from midpoint angle 'B' on a marked linear path to midpoint angle 'A'; and from midpoint angle 'A' on a marked linear path to the end-point angle 'C' (formerly starting-point angle 'C').

The person can simultaneously and/or independently move the computerized cursors by the physical gestures of both the hands and the feet (extremities). The display counter will record and display the speed, deviation and accuracy of the extremities in a pattern. The performance data (speed, deviation and accuracy) results are displayed in the pattern after the cursor arrives at the ending-point angle 'A', ideally, at the same time. The displayed results of the cursor allow the person to compare the competitiveness of the extremity against the other. Repeating the exercise improves the speed results of the extremity and prepares the person for the next exercise template which employs a different pattern and skill set.

Figure 6:
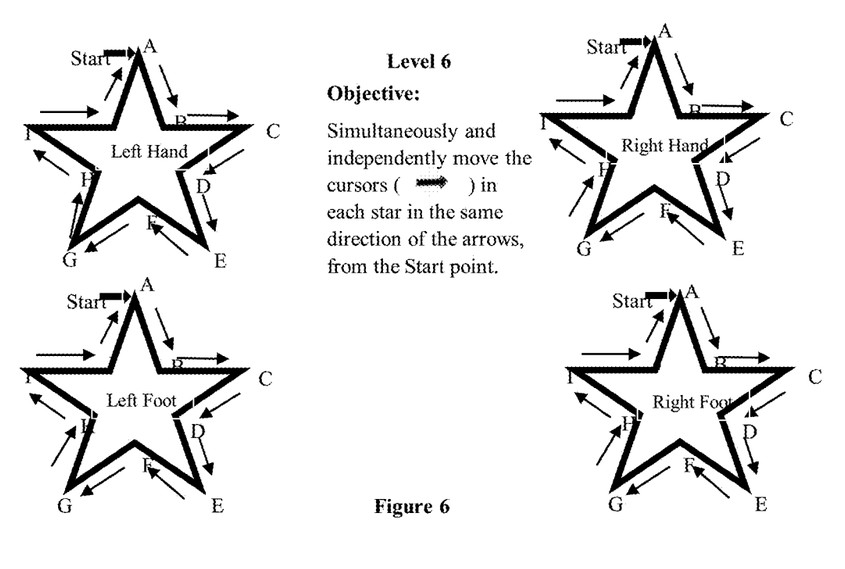
FIG. 6. Simultaneously and/or independently move the cursors in the pentagram clockwise in each star in the same direction of the arrows by using the left-hand, right-hand, left-foot, right-foot; Start from AB C D E F G H I-J-A FIG. 7. Simultaneously and/or independently move the cursors counter-clockwise in each star in the same direction of the arrows by using the left-hand, right-hand, left-foot and right-foot; Start from G F E D C B A J-I-H-G FIG. 8. Pictorial embodiment of invention with numerical identifiers

FIG. 6 template (level 6) illustrates the template with four identical pentagram exercise patterns with an equal number of pixels that are displayed on the computer screen by the HMI exercise pattern application. The pattern is for the left-hand, the pattern is for the right-hand, the pattern is for the left-foot and the pattern is for the right-foot. The pattern displays a two-dimensional colored blinking computerized cursor which is located on the top angle 'A' of a pattern, and a specific path for the cursor to traverse. The cursor path in each pentagram pattern traverses from a starting-point angle 'A' to midpoint angle 'B'; from midpoint angle 'B' to midpoint angle 'C'; from midpoint angle 'C' to midpoint angle 'D'; from midpoint angle 'D' to midpoint angle 'E'; from midpoint angle 'E' to midpoint angle 'F', from midpoint angle 'F' to midpoint angle 'G'; from midpoint angle 'G' to midpoint angle 'H'; from midpoint angle 'H' to midpoint angle 'I'; from midpoint angle 'I' to midpoint angle 'J'; and from midpoint angle 'J' to the end-point angle 'A' (formerly starting-point angle 'A'). Once the person appends the mice to the extremities as discussed in paragraph [0015] and clicks on the HMI exercise pattern application icon, chooses the exercise template and selects the displayed ready message 'YES', activates the exercise application of cognitive abilities. After activation of the pattern application, the person can now start to simultaneously and/or independently move the top angle 'A' cursor in the pattern from starting-point angle 'A' to the ending-point angle 'A' by the physical gestures of the extremities. When FIG. 6 template application is activated, and the person appends the mice to the extremities, a person can:

Reference left-hand pentagram pattern: move blue blinking cursor #1, located at top angle 'A' of the left-hand pentagram pattern, on a marked linear path from starting-point angle 'A' to midpoint angle 'B'; from midpoint angle 'B' on a marked linear path to midpoint angle 'C'; from midpoint angle 'C' on a marked linear path to midpoint angle 'D'; from midpoint angle 'D' on a marked linear path to midpoint angle 'E'; from midpoint angle 'E' on a marked linear path to midpoint angle 'F'; from midpoint angle 'F' on a marked linear path to midpoint angle 'G'; from midpoint angle 'G' on a marked linear path to midpoint angle 'H'; from midpoint angle 'H' on a marked linear path to midpoint angle 'I'; from midpoint angle 'I' on a marked linear path to midpoint angle 'J'; and from midpoint angle 'J' on a marked linear path to the end-point angle 'A' (formerly starting-point angle 'A').

Reference right-hand pentagram pattern: move green blinking cursor #2, located at top angle 'A' of the right-hand pentagram pattern, on a marked linear path from starting-point angle 'A' to midpoint angle 'B'; from midpoint angle 'B' on a marked linear path to midpoint angle 'C'; from midpoint angle 'C' on a marked linear path to midpoint angle 'D'; from midpoint angle 'D' on a marked linear path to midpoint angle 'E'; from midpoint angle 'E' on a marked linear path to midpoint angle 'F'; from midpoint angle 'F' on a marked linear path to midpoint angle 'G'; from midpoint angle 'G' on a marked linear path to midpoint angle 'H'; from midpoint angle 'H' on a marked linear path to midpoint angle 'I'; from midpoint angle 'I' on a marked linear path to midpoint angle 'J'; and from midpoint angle 'J' on a marked linear path to the end-point angle 'A' (formerly starting-point angle 'A').

Reference left-foot pentagram pattern: move yellow blinking cursor #3, located at top angle 'A' of the left-foot pentagram pattern, on a marked linear path from starting-point angle 'A' to midpoint angle 'B'; from midpoint angle 'B' on a marked linear path to midpoint angle 'C'; from midpoint angle 'C' on a marked linear path to midpoint angle 'D'; from midpoint angle 'D' on a marked linear path to midpoint angle 'E'; from midpoint angle 'E' on a marked linear path to midpoint angle 'F'; from midpoint angle 'F' on a marked linear path to midpoint angle 'G'; from midpoint angle 'G' on a marked linear path to midpoint angle 'H'; from midpoint angle 'H' on a marked linear path to midpoint angle 'I'; from midpoint angle 'I' on a marked linear path to midpoint angle 'J'; and from midpoint angle 'J' on a marked linear path to the end-point angle 'A' (formerly starting-point angle 'A').

Reference right-foot pentagram pattern: move red blinking cursor #4, located at top angle 'A' of the right-foot pentagram pattern, on a marked linear path from starting-point angle 'A' to midpoint angle 'B'; from midpoint angle 'B' on a marked linear path to midpoint angle 'C'; from midpoint angle 'C' on a marked linear path to midpoint angle 'D'; from midpoint angle 'D' on a marked linear path to midpoint angle 'E'; from midpoint angle 'E' on a marked linear path to midpoint angle 'F'; from midpoint angle 'F' on a marked linear path to midpoint angle 'G'; from midpoint angle 'G' on a marked linear path to midpoint angle 'H'; from midpoint angle 'H' on a marked linear path to midpoint angle 'I'; from midpoint angle 'I' on a marked linear path to midpoint angle 'J'; and from midpoint angle 'J' on a marked linear path to the end-point angle 'A' (formerly starting-point angle 'A').

FIG. 7 template (level 7) illustrates a template with four identical pentagram exercise patterns with an equal number of pixels that is displayed on a computer screen by an HMI exercise pattern application. A pattern is for a left-hand, a pattern is for a right-hand, a pattern is for a left-foot and a pattern is for a right-foot. A pattern displays two-dimensional colored blinking computerized cursors which are located on the mid-point angle 'G' of the pattern, and a specific path for a cursor to traverse. A cursor path in each pentagram pattern traverses from the starting-point angle 'G' to midpoint angle 'F'; from midpoint angle 'F' to midpoint angle 'E'; and midpoint angle 'E' to midpoint angle 'D'; from midpoint angle 'D' to midpoint angle 'C'; from midpoint angle 'C' to midpoint angle 'B', from midpoint angle 'B' to midpoint angle 'A': from midpoint angle 'A' to midpoint angle 'J'; from midpoint angle 'J' to midpoint angle 'I'; from midpoint angle 'I' to midpoint angle 'H'; and from midpoint angle 'H' to the end-point angle 'G' (formerly starting-point 'G'). Once the user appends the mice to the extremities as discussed in paragraph [0015] and clicks on the HMI exercise pattern application icon, chooses an exercise template and selects the displayed ready message 'YES', activates the exercise application of cognitive abilities. After activation of the pattern application, the person can now start to simultaneously and/or independently move the mid-point angle 'G' cursor in the pattern from starting-point angle 'G' to the ending-point angle 'G' by the physical actions of the four extremities. When FIG. 7 template application is activated, and a user appends the mice to the extremities, the person can:

Reference left-hand pentagram pattern: move blue blinking cursor #1, located at mid-point angle 'G' of the left-hand pentagram pattern, and on a marked linear path from starting-point angle 'G' to midpoint angle 'F'; from midpoint angle 'F' on a marked linear path to midpoint angle 'E'; from midpoint angle 'E' on a marked linear path to midpoint angle 'D'; from midpoint angle 'D' on a marked linear path to midpoint angle 'C'; from midpoint angle 'C' on a marked linear path to midpoint angle 'B'; from midpoint angle 'B' on a marked linear path to midpoint angle 'A'; from midpoint angle 'A' on a marked path to midpoint angle 'J'; from midpoint angle 'J' on a marked linear path to midpoint angle 'I'; from midpoint angle 'I' on a marked linear path to midpoint angle 'H'; and from midpoint angle 'H' on a marked linear path to the end-point angle 'G' (formerly starting-point angle 'G').

Reference right-hand pentagram pattern: move green blinking cursor 2, located at midpoint angle 'G' of the right-hand pentagram pattern, and on a marked linear path from starting-point angle 'G' to midpoint angle 'F'; from midpoint angle 'F' on a marked linear path to midpoint angle 'E'; from midpoint angle 'E' on a marked linear path to midpoint angle 'D'; from midpoint angle 'D' on a marked linear path to midpoint angle 'C'; from midpoint angle 'C' on a marked linear path to midpoint angle 'B'; from midpoint angle 'B' on a marked linear path to midpoint angle 'A'; from midpoint angle 'A' on a marked path to midpoint angle 'J'; from midpoint angle 'J' on a marked linear path to midpoint angle 'I'; from midpoint angle 'I' on a marked linear path to midpoint angle 'H'; and from midpoint angle 'H' on a marked linear path to the end-point angle 'G' (formerly starting-point angle 'G')

Reference left-foot pentagram pattern: move yellow blinking cursor 3, located at top angle 'G' of the left-foot pentagram pattern, and on a marked linear path from starting-point angle 'G' to midpoint angle 'F'; from midpoint angle 'F' on a marked linear path to midpoint angle 'E'; from midpoint angle 'E' on a marked linear path to midpoint angle 'D'; from midpoint angle 'D' on a marked linear path to midpoint angle 'C'; from midpoint angle 'C' on a marked linear path to midpoint angle 'B'; from midpoint angle 'B' on a marked linear path to midpoint angle 'A'; from midpoint angle 'A' on a marked path to midpoint angle 'J'; from midpoint angle 'J' on a marked linear path to midpoint angle 'I'; from midpoint angle 'I' on a marked linear path to midpoint angle 'H'; and from midpoint angle 'H' on a marked linear path to end-point angle 'G' (formerly starting-point angle 'G').

Reference right-foot pentagram pattern: move red blinking cursor 4, located at top angle 'G' of the right-foot pentagram pattern, and on a marked linear path from starting-point angle 'G' to midpoint angle 'F'; from midpoint angle 'F' on a marked linear path to midpoint angle 'E'; from midpoint angle 'E' on a marked linear path to midpoint angle 'D'; from midpoint angle 'D' on a marked linear path to midpoint angle 'C'; from midpoint angle 'C' on a marked linear path to midpoint angle 'B'; from midpoint angle 'B' on a marked linear path to midpoint angle 'A'; from midpoint angle 'A' on a marked path to midpoint angle 'J'; from midpoint angle 'J' on a marked linear path to midpoint angle 'I'; from midpoint angle 'I' on a marked linear path to midpoint angle 'H'; and from midpoint angle 'H' on a marked linear path to the end-point angle 'G' (formerly starting-point angle 'G').

The person can simultaneously and/or independently move the computerized cursors by the physical gestures of both the hands and the feet (extremities). The display counter will record and display the speed, deviation and accuracy of the extremity of the cursor in the pattern. The performance data (speed, deviation and accuracy) results are displayed in the pattern during and after the cursor arrives at the ending-point angle 'G', ideally, at the same time. The displayed results of the cursor allow the person to compare the competitiveness of the extremity against the other. Repeating the exercise improves the speed and accuracy of the extremity and prepares the user for the next exercise template which employs a different pattern and skill set.

The invention claimed is:

1. An apparatus for moving four computerized cursors simultaneously by corresponding gestures controlled by a person's left-hand, right-hand, left-foot and right-foot, said apparatus comprising:
   a left-hand mouse controlled by the left-hand to manipulate a first cursor of the four computerized cursors,
   a right-hand mouse controlled by the right-hand to manipulate a second cursor of the four computerized cursors,
   a left-foot mouse controlled by the left-foot to manipulate a third cursor of the four computerized cursors, and
   a right-foot mouse controlled the right foot to manipulate a fourth cursor of the four computerized cursors;
   a computer to communicate with the person, said computer comprising:
   a) a processor to monitor, analyze, calculate, record, and transmit real-time movement data of said four computerized cursors,
   b) a memory to store said real-time movement data,
   c) a display to exhibit said real-time movement data,
   d) four USB ports connected to the left-hand mouse, right-hand mouse, left-foot mouse and right-foot mouse with a one-to-one correspondence; and
   e) a cognitive human-man-interface (HMI) application to instruct the person to execute the movement of said four computerized cursors simultaneously on a pattern of a plurality of patterns of various skill levels, wherein the exercise apparatus will enhance mental agility of the person by simultaneously moving said four computerized cursors on said pattern from a starting-point to a target in the fastest time possible;
   wherein the processor and the memory transmit said real-time movement data of said four computerized cursors in real-time to four cursor counters on said display wherein each cursor counter is associated with one of the four cursors and simultaneously displays the cursor movement data by gestures of the right-hand mouse, left-hand mouse, left-foot mouse and right-foot mouse; said cursor data movement counters displaying: a) said cursors speed, b) said cursors completion time, c) said cursors path deviation, d) said cursors distance, and e) said cursors accuracy of the left-hand mouse, right-hand mouse, left-foot mouse, and right-foot mouse.

2. The apparatus of claim 1, wherein said cursor counters are located at the top left, top right, bottom left, bottom right of said display,
   wherein said four computerized cursors can be assigned a specific color and can blink; and
   wherein said plurality of patterns includes seven patterns of various skill levels.

3. The apparatus of claim 1, wherein said left-hand mouse, said right-hand mouse, said left-foot mouse, and said right-foot mouse are connected hard-wired or wirelessly to said four USB ports and said left-hand mouse, said right-hand mouse, said left-foot mouse, and said right-foot mouse are appended to the person's left-hand, right-hand, left-foot and right-foot, respectively.

* * * * *